United States Patent
Szucs et al.

(10) Patent No.: US 6,465,395 B2
(45) Date of Patent: Oct. 15, 2002

(54) SUBSTITUTED METHYLENE PYRAZOLINONES AND THE HERBICIDAL USE THEREOF

(75) Inventors: Stephen S. Szucs; Kun-Jian Gu, both of Lawrenceville, NJ (US)

(73) Assignees: BASF Aktiengesellschaft, Ludwigshafen (DE); Idemitsu Kosan Company, Ltd., Tokyo (JP)

( * ) Notice: Subject to any disclaimer, the term of this patent is extended or adjusted under 35 U.S.C. 154(b) by 0 days.

(21) Appl. No.: 09/796,163

(22) Filed: Feb. 28, 2001

(65) Prior Publication Data
US 2002/0016261 A1 Feb. 7, 2002

Related U.S. Application Data

(60) Provisional application No. 60/186,103, filed on Mar. 1, 2000.

(51) Int. Cl.$^7$ .................. C07D 231/20; C07D 407/06; C07D 409/06; A01N 43/56
(52) U.S. Cl. .................. 504/282; 548/364.4; 504/253; 504/219; 546/202; 546/196; 540/603
(58) Field of Search ................. 548/365.1, 364.4; 514/404; 504/139, 282, 253; 546/202; 540/603

(56) References Cited

U.S. PATENT DOCUMENTS 5,607,898 A  3/1997  Nakamura et al. .......... 504/282

FOREIGN PATENT DOCUMENTS

| CA | 2333234 | 11/1999 | ......... C07D/409/06 |
|----|---------|---------|------------------------|
| WO | WO 97/08164 | 3/1997 | |
| WO | WO 98/35954 | 8/1998 | |
| WO | WO 99/26930 | 6/1999 | |
| WO | WO 99/59991 | 11/1999 | |
| WO | WO-99/59991 | * 11/1999 | |

* cited by examiner

Primary Examiner—John M. Ford
(74) Attorney, Agent, or Firm—Keil & Weinkauf

(57) ABSTRACT

The present invention provides thiochroman- and dihydrobenzothiophene-substituted methylene compounds of formula I.

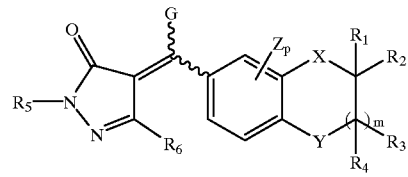

(I)

Further provided are compositions and methods utilizing said formula I compounds for the control of undesirable plant species.

19 Claims, No Drawings

SUBSTITUTED METHYLENE PYRAZOLINONES AND THE HERBICIDAL USE THEREOF

This application claims the benefit under 35 U.S.A 119(e) of provisional application 60/186,103 filed Mar. 1, 2000.

BACKGROUND OF THE INVENTION

Weeds cause tremendous global economic losses by reducing crop yields and lowering crop quality. Worldwide, agronomic crops must compete with a vast variety of weed species. Although there are a number of commercial herbicides available, crop safety and efficacy over a broad spectrum of weed species remain challenges in modern agronomic practice. Accordingly there is an ongoing need to discover and develope more crop-selective and broader spectrum herbicidal agents.

Thiochroman- and dihydrobenzothiophene-hydroxypyrazole derivatives and their herbicidal use are described in U.S. Pat. No. 5,607,898 and WO 97/08164. However, thiochroman and dihydrobenzothiophene substituted methylene pyrazolinone compounds and their use as broad-spectrum, crop-selective herbicides are not described therein.

Therefore, it is an object of this invention to provide highly effective broad spectrum herbicidal methylene pyrazolinone compounds.

It is also an object of this invention to provide a method for the control of a broad spectrum of undesirable plant species.

It is a further object of this invention to provide a method for the selective control of undesirable plant species in the presence of a crop.

These and other objects and features of the invention will become more apparent from the detailed description thereof set forth hereinbelow.

SUMMARY OF THE INVENTION

The present invention provides thiochroman-and dihydrobenzothiophene-substituted methylene pyrazolinone compounds of formula I

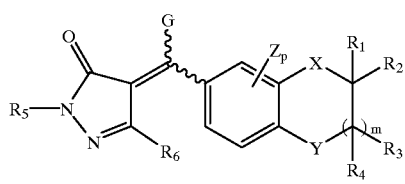

wherein m is zero or 1;

$R_1$, $R_2$, $R_3$ and $R_4$ are each independently H, $C_1$–$C_4$ alkyl, $C_1$–$C_4$ haloalkyl or $C_2$–$C_4$ alkoxyalkyl;

$R_5$ is $C_1$–$C_3$ alkyl, $C_3$–$C_4$ alkenyl or $C_3$–$C_4$ haloalkenyl;

$R_6$ is H, halogen, CN, $C_1$–$C_4$ alkyl, $C_2$–$C_4$ alkenyl, $C_1$–$C_4$ alkoxyalkyl or $C_1$–$C_4$ alkoxycarbonyl;

X is $CR_7R_8$, $CHOR_9$, $C=NOR_{10}$, $C=NNR_{16}R_{17}$, $C=O$ or $C(OR_9)_2$;

$R_7$ is H, $C_1$–$C_4$ alkyl or $C_1$–$C_4$ haloalkyl;

$R_8$ is H, $C_1$–$C_4$ alkyl, $C_2$–$C_4$ alkenyl, $C_2$–$C_4$ alkynyl or $C_1$–$C_4$ alkoxyalkyl;

$R_9$ and $R_{10}$ are each independently H or $C_1$–$C_6$ alkyl optionally substituted with one or more $C_2$–$C_6$ alkenyl, $C_2$–$C_6$ alkynyl, $C_1$–$C_6$ haloalkyl or $C_3$–$C_6$ cycloalkyl groups;

Y is O, S, SO or $SO_2$;

Z is H, halogen, $C_1$–$C_4$ alkyl, $C_1$–$C_4$ haloalkyl, $C_2$–$C_4$ alkoxyalkyl, $C_1$–$C_4$ alkoxy or $C_1$–$C_4$ haloalkoxy;

p is an integer of 1, 2 or 3;

G is $OR_{11}$, $OCH_2COR_{11}$, $SCH_2COR_{11}$, $OCN_2CSR_{11}$, $SCH_2CSR_{11}$, $OCOR_{11}$, $SCOR_{11}$, $OCSR_{11}$, $SCSR_{11}$, $S(O)_n R_{12}$, $NR_{13}R_{14}$, $P(O) (OR_{15})_2$, halogen, CN, SCN,

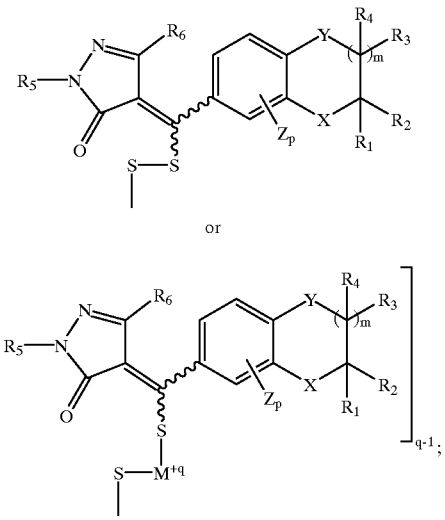

n is zero, 1 or 2;

$R_{11}$ and $R_{12}$ are each independently $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_1$–$C_6$ alkoxyalkyl, benzyl optionally substituted with one to three halogen, $C_1$–$C_6$ alkyl, $C_1$–$C_6$ alkoxy or $C_1$–$C_6$ haloalkyl groups or phenyl optionally substituted with one to three halogen, $C_1$–$C_6$ alkyl, $C_1$–$C_6$ alkoxy or $C_1$–$C_6$ haloalkyl groups;

$R_{13}$ and $R_{14}$ are each independently H, $C_1$–$C_6$ alkyl, $C_3$–$C_6$ alkenyl, $C_3$–$C_6$ alkynyl, or $R_{13}$ and $R_{14}$ may be taken together with the atom to which they are attached to represent a four- to seven-membered ring optionally interrupted by oxygen, sulfur, or nitrogen and optionally substituted with one to three halogen or $C_1$–$C_6$ alkyl groups;

$R_{15}$ is $C_1$–$C_6$ alkyl;

$R_{16}$ is H or $C_1$–$C_6$ alkyl;

$R_{17}$ is H, $C_1$–$C_6$ alkyl, $C_1$–$C_6$ haloalkyl, $C_2$–$C_6$ alkoxycarbonyl, $C_2$–$C_6$ alkylcarbonyl, $COR_{18}$ or phenyl optionally substituted with one to three $C_1$–$C_3$ alkyl, halogen, CN or $NO_2$ groups, or $R_{16}$ and $R_{17}$ may be taken together to represent $=C(C_1$–$C_3$ alkyl$)_2$;

$R_{18}$ is phenyl optionally substituted with one to three $C_1$–$C_3$ alkyl, halogen, CN or $NO_2$ groups, or a 5-to 6-membered aromatic heterocyclic ring optionally substituted with one to three $C_1$–$C_3$ alkyl, halogen, CN or $NO_2$ groups;

M is a transition metal or an alkaline-earth metal; and q is an integer of 1, 2 or 3; or the geometric or optically active isomers thereof.

The present invention also provides herbicidal compositions and methods and a process to prepare a compound of formula I.

DETAILED DESCRIPTION OF THE INVENTION

Good pest management practice requires new herbicidal agents which demonstrate efficacy toward a broad spectrum of undesirable monocotyledenous and dicotyledenous plant species and preferably also demonstrate crop safety.

Surprisingly it has now been found that thiochroman and dihydrobenzothiophene derivatives of methylene pyrazolinone compounds of formula I demonstrate a broad spectrum of weed control along with acceptable or good crop safety. In particular said methylene pyrazolinone formula I compounds are surprisingly safe in cereal crops such as corn, wheat, rice, or the like, preferably corn.

The compounds of the invention have the structural formula I

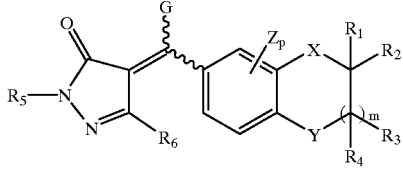

(I)

wherein $R_1$, $R_2$, $R_3$, $R_4$, $R_5$, $R_6$, G, X, Y, Z, m and p, are as defined hereinabove for formula I.

Preferred methylene pyrazolinone compounds of the invention are those compounds of formula I wherein $R_1$, $R_2$, $R_3$ and $R_4$ are each independently H or $C_1$–$C_4$ alkyl;

$R_5$ is $C_1$–$C_3$ alkyl;

$R_6$ is H or $C_1$–$C_4$ alkyl;

X is $CR_7R_8$ or $C=NOR_{10}$;

$R_7$ and $R_8$ are each independently H or $C_1$–$C_4$ alkyl;

$R_{10}$ is H or $C_1$–$C_6$ alkyl;

Y is $SO_2$;

Z is H, halogen or $C_1$–$C_4$ alkyl;

G is $OR_{11}$, $S(O)_nR_{12}$, $NR_{13}R_{14}$,

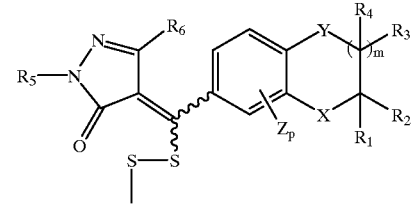

or

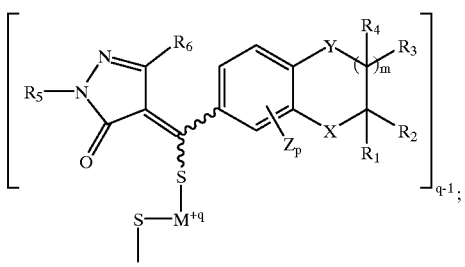

n is zero, 1 or 2;

$R_{11}$ and $R_{12}$ are each independently $C_1$–$C_6$ alkyl or phenyl optionally substituted with one to three halogen, $C_1$–$C_6$alky, $C_1$–$C_6$ alkoxy, or $C_1$–$C_6$ haloalkyl groups; and $R_{13}$ and $R_{14}$ are each independently H or phenyl optionally substituted with one to three halogen, $C_1$–$C_6$alkyl, $C_1$–$C_6$alkoxy or $C_1$–$C_6$haloalkyl groups.

More preferred compounds of the invention are those compounds of formula I wherein m is zero;

$R_1$ and $R_2$ are H;

$R_5$ is $C_1$–$C_3$ alkyl;

$R_6$ is H;

X is $CR_7R_8$;

$R_7$ and $R_8$ are each independently $C_1$–$C_4$ alkyl;

Y is $SO_2$;

Z is $C_1$–$C_4$ alkyl;

p is 1 or 2;

G is $OR_{11}$, $S(O)_nR_{12}$,

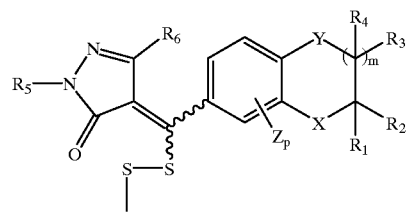

or

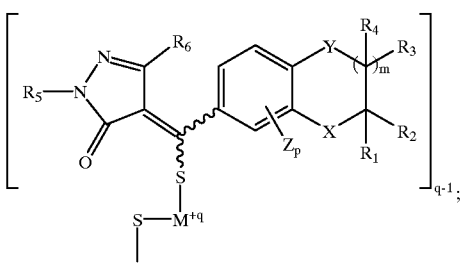

n is zero or 2;

$R_{11}$ is phenyl optionally substituted with one to three halogen, $C_1$–$C_2$ alkyl, $C_1$–$C_3$ alkoxy or $C_1$–$C_3$ haloalkyl groups; and $R_{12}$ is $C_1$–$C_6$ alkyl, $C_1$–$C_3$alkoxyalkyl or $C_1$–$C_3$haloalkyl.

Particularly preferred compounds of the invention are those compounds of formula I wherein m is 1;

$R_1$, $R_2$, $R_3$ and $R_4$ are H;

$R_5$ is $C_1$–$C_3$ alkyl;

$R_6$ is H;

X is $C=NOR_{10}$;

$R_{10}$ is $C_1$–$C_6$ alkyl;

Z is $C_1$–$C_4$ alkyl;

p is 1 or 2;

G is $OR_{11}$, $S(O)_nR_{12}$,

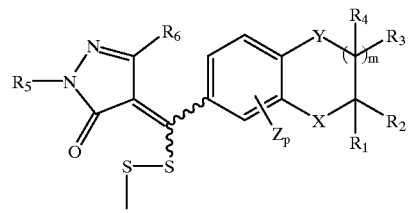

or

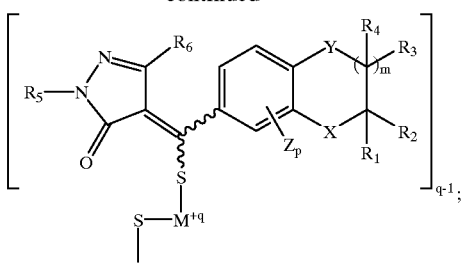

n is zero or 2;

$R_{11}$ is phenyl optionally substituted with one to three halogen, $C_1$–$C_2$ alkyl, $C_1$–$C_3$ alkoxy, or $C_1$–$C_3$ haloalkyl groups; and $R_{12}$ is $C_1$–$C_6$ alkyl, $C_1$–$C_3$ alkoxyalkyl or $C_1$–$C_3$ haloalkyl.

The term halogen as used in the specification and claims designates chlorine, fluorine, bromine or iodine. The term haloalkyl designates an alkyl group, $C_nH_{2n+1}$ which may contain from one halogen atom to 2n+1 halogen atoms. Similarly, the term haloalkoxy designates a $OC_nH_{2n+1}$ group which may contain from one to 2n+1 halogen atoms. Haloalkenyl designates an alkenyl group $C_nH_{2n}$ which may contain from one to 2n halogen atoms. In each instance the halogen atoms may be the same or different. Similarly, the term $C_1$–$C_3$ alkoxyalkyl designates a $C_1$–$C_6$ alkyl group substituted with one or more $C_1$–$C_3$ alkoxy groups which may be the same or different.

The term transition metal as used in the specification and claims designates zinc, copper, iron, manganese, titanium, nickel, or any of the commonly occurring transition elements listed in Groups IB through VIIIB on the periodic chart. Similarly, the term alkaline-earth metal designates magnesium, calcium, strontium, barium or any of the commonly occurring alkaline-earth elements listed in Group IIA on the periodic chart.

Compounds of formula I may exist in enolic tautomeric forms that may give rise to geometric isomers around the enolic double bond. The wavy lines in structural formula I represent the interchangeability of the G moiety and the bicyclic structure around the methine carbon, i.e. the E isomeric or the Z isomeric configuration. Further, structural formula I may include one or more assymetric carbon atoms, giving rise to stereoisomeric forms. All such geometric and stereoisomeric forms of the compound of formula I are embraced by the present invention.

Among the formula I compounds of the invention which are particularly effective herbicidal agents are:

1-Ethyl-4–[(E)-(5-methyl-4-oxothiochroman-6-yl) (propylthio)methylene]-2-pyrazolin-5-one 4'-[(E)-O-methyloxime], S,S-dioxide;

1-Ethyl-4-[(Z)-(5-methyl-4-oxothiochroman-6-yl) (propylthio)methylene]-2-pyrazolin-5-one 4'-[(E)-O-methyloxime], S,S-dioxide;

1-Ethyl-4-[(E)-(5-methyl-4-oxothiochroman-6-yl) (propylsulfonyl)methylene]-2-pyrazolin-5-one 4'-[(E)-O-methyloxime], S,S-dioxide;

1-Ethyl-4-[(Z)-(5-methyl-4-oxothiochroman-6-yl) (propylsulfonyl)methylene]-2-pyrazolin-5-one 4'-[(E)-O-methyloxime}, S,S-dioxide;

4,4'-[(Z,Z)-Dithiobis[(2,3-dihydro-3,3,4-trimethylbenzo [b]thien-5-yl)methylidyne]]bis[1-methyl-2-pyrazolin-5-one] S,S,S',S'-tetraoxide;

4,4'-[(E,Z)-Dithiobis[(2,3-dihydro-3,3,4-trimethylbenzo [b]thien-5-yl)methylidyne]]bis[1-methyl-2-pyrazolin-5-one] S,S,S',S'-tetraoxide;

4-[(Z)-(2,3-Dihydro-3,3,4-trimethylbenzo [b] thien-5-yl) (propylthio)methylene]-1-methyl-2-pyrazolin-5-one S,S-dioxide;

4-{(Z)-(2,3-Dihydro-3,3,4-trimethylbenzo [b] thien-5-yl) [(m-trifluoromethyl)anilino]methylene}-1-methyl-2-pyrazolin-5-one S,S-dioxide;

4-[(Z)-(2,3-Dihydro-3,3,4-trimethylbenzo[b]thien-5-yl) (p-methoxyphenoxy)methylene]-1-methyl-2-pyrazolin-5-one S,S-dioxide; or the like.

Formula I compounds wherein G is $OR_{11}$ or $SR_{12}$ may be prepared by reacting the chloro compound of formula Ia with a hydroxy compound $R_{11}OH$ or a thiol $R_{12}SH$, respectively, in the presence of a base. The reaction is shown in flow diagram I.

FLOW DIAGRAM I

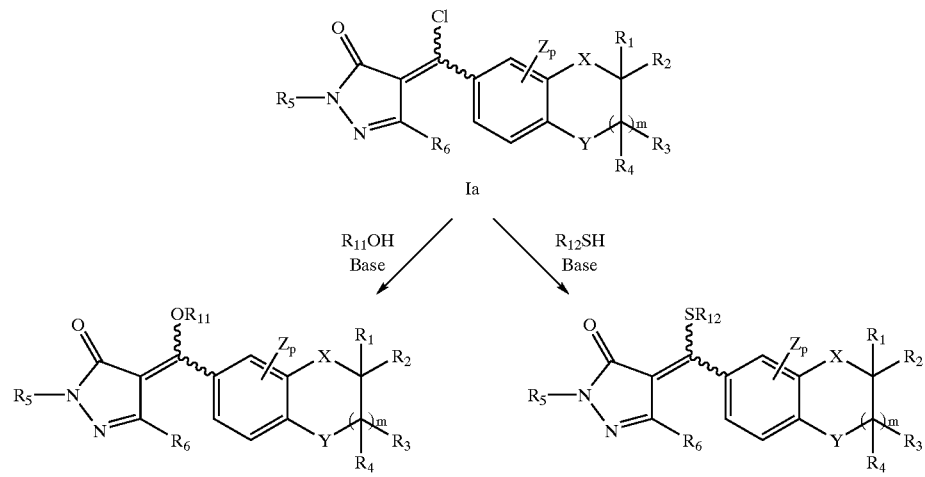

The chloro compound of formula Ia may be prepared by reacting an alkylsulfonate of formula II with an aroyl chloride ArCOCl as shown in Flow Diagram II.

FLOW DIAGRAM II

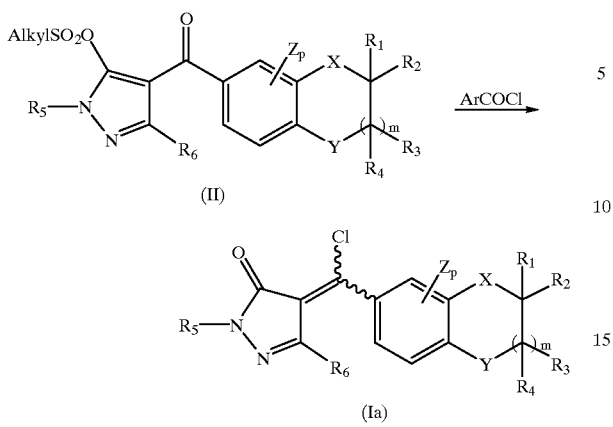

Alternatively, the compound of formula I wherein G is $SR_{12}$ may be prepared by the conversion of a ketone of formula III to a thioketone of formula IV with Lawesson's reagent, and alkylating said thioketone with an alkylating agent $R_{12}Z_1$ wherein $Z_1$ is Cl, Br or I, in the presence of a base. Compounds of formula I wherein G is $SR_{12}$ may be oxidized to the corresponding sulfoxide or sulfone derivative with one or two molar equivalents of an oxidant such as m-chloroperbenzoic acid. The reactions are shown in Flow Diagram III.

FLOW DIAGRAM III

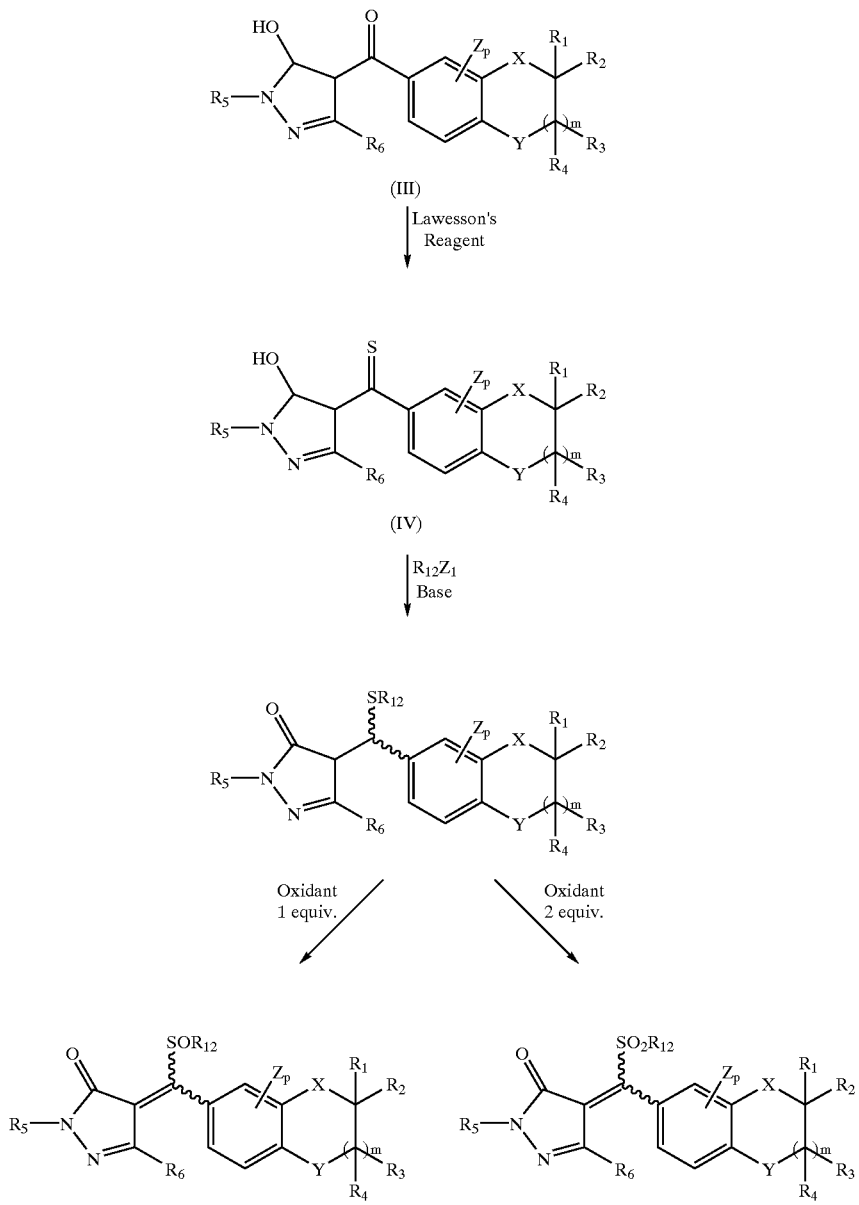

Compounds of formula II and formula III and methods for their preparation are described in U.S. Pat. No. 5,607,898 and WO 97/08164.

The compound of formula I wherein G is

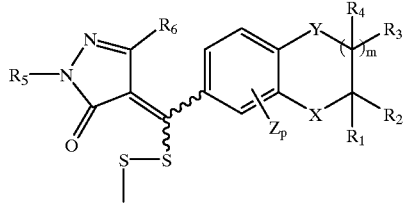

may be prepared by direct oxidation of a thioketone of formula IV as shown in Flow Diagram IV.

FLOW DIAGRAM IV

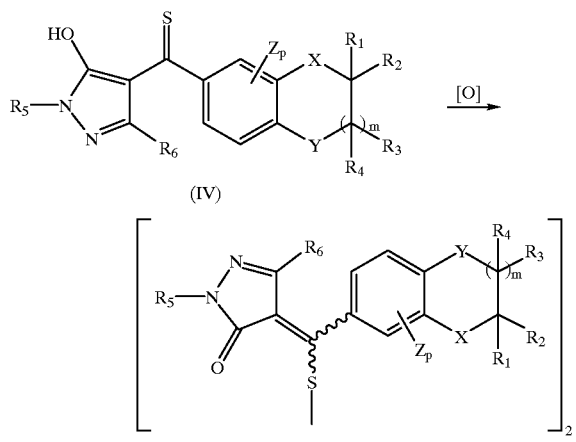

Compounds of formula I wherein G is

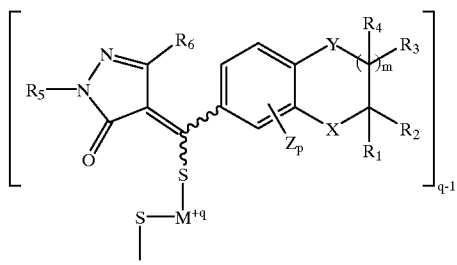

may be prepared by treatment of a thione of formula IV with a transition metal or alkaline-earth metal salt $M^{+q}(X_1)_q$, wherein $X_1$ is a halide, acetate or nitrate anion, in the presence of an acid or a base as shown in Flow Diagram V.

FLOW DIAGRAM V

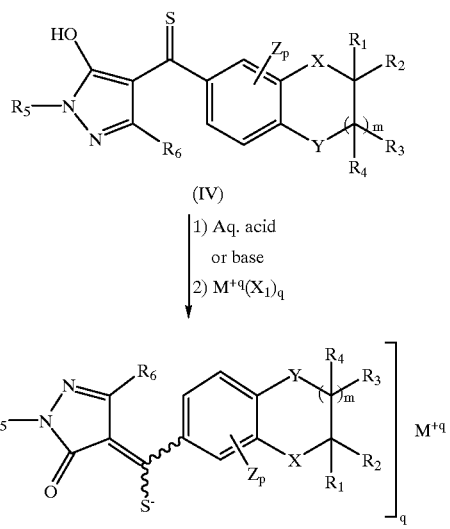

Compound I wherein G is $NR_{13}R_{14}$ may be prepared by reacting the chloro compound of formula Ia with an amine $HNR_{13}R_{14}$, in the presence of a base, as depicted in Flow Diagram VI.

FLOW DIAGRAM VI

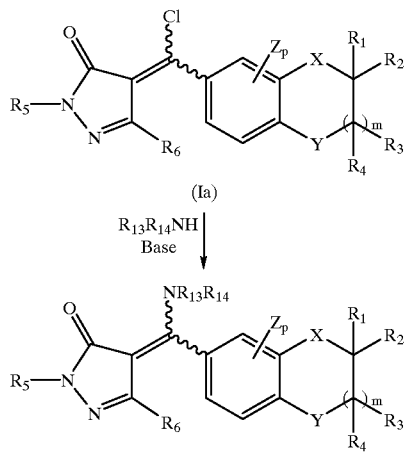

Compound I wherein G is $P(O)(OR_{15})_2$ may be prepared by treating chloro compound Ia with a phosphite $P(OR_{15})_3$ as depicted in Flow Diagram VII.

FLOW DIAGRAM VII

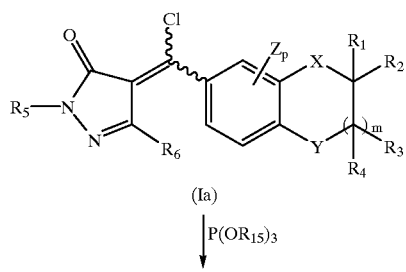

-continued

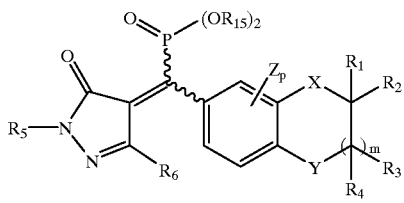

Advantageously, it has been found that the formula I compounds of the invention are particularly useful for the control of undesirable monocotyledenous and dicotyledenous plant species. Surprisingly, the compounds of this invention demonstrate selective weed control in cereal crops such as corn, wheat, rice, or the like preferably corn or rice.

In actual practice, compounds of the invention may be applied to the foliage of undesirable plant species or to the soil or water containing seeds or other propagating organs thereof in the form of a solid or liquid herbicidal composition. Compositions of the invention comprise a herbicidally effective amount of the compound of formula I dispersed or dissolved in an agronomically acceptable inert solid or liquid carrier. Herbicidally effective amounts may vary according to the prevailing conditions such as weed pressure, crop species, application timing, soil conditions, weather conditions and the like. In general, amounts sufficient to selectively control weeds are obtained when the formula I compound is applied at rates of about 0.001 kg/ha to 10.0 kg/ha, preferably about 0.003 to 0.50 kg/ha, more preferably about 0.006 to 0.20 kg/ha.

The composition of the present invention may take the form of an emulsifiable concentrate, a concentrated emulsion, a microemulsion, a wettable powder, a soluble granule, a suspension concentrate, a flowable concentrate or any convenient conventional form useful for herbicide application.

The composition of the invention may be applied in combination with other herbicides such as dinitroanlines, for example trifluralin, pendimethalin or the like; triazines, for example atrazine, cyanazine, metribuzin or the like; AHAS inhibitors for example imidazolinones, sulfonyl ureas or the like; protox inhibitors; or any of the commonly employed, commercially available herbicidal agents. Said combination may be applied sequentially or concurrently as a tank-mix or co-formulation. Compositions of the invention embrace compounds of formula I alone or in combination with a second herbicide as active ingredient.

In order to facilitate a further understanding of the invention, the following examples are presented to illustrate more specific details thereof. The invention is not to be limited thereby except as defined in the claims. The terms $^1$HNMR and $^{13}$CNMR designate proton and carbon NMR respectively, and the terms IR and MS designate infrared spectrometry and mass spectroscopy, respectively.

EXAMPLE 1

Preparation of 4-[(Z)-Chloro-(2,3-dihydro-3,3,4-trimethylbenzo[b]thien-5-yl)methylene]-1-methyl-2-pyrazolin-5-one S,S-dioxide

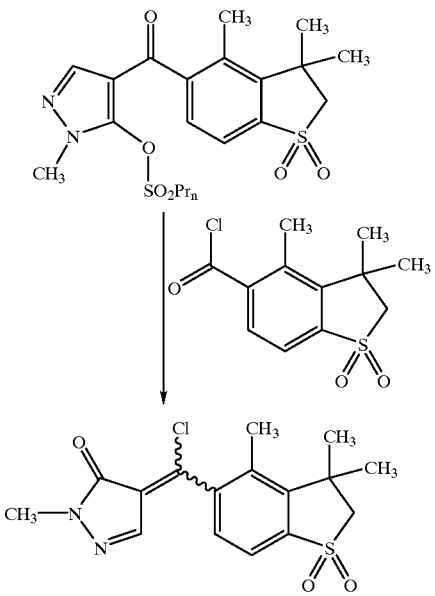

A solution of 2,3-dihydro-5-[(5-hydroxy-1-methylpyrazol-4-yl)carbonyl]-3-3-4-trimethylbenzo[b]thiophene propanesulfonate 1,1-dioxide (0.160 g, 0.36 mmol) in methylene chloride is treated with a solution of (3,3,4-trimethylbenzo[b]thien-5-yl)-5-carboxylic acid chloride in methylene chloride, heated in a sealed pressure vial at 60–70° C. for 24 hr, cooled, diluted with methylene chloride and chromatographed on silica gel with methylene chloride to give a crude solid. Crystallization of the solid with methanol affords the title compound as a yellow solid (0.100 g, 78%, mp 195–197° C.), characterized by IR, $^1$HNMR, $^{13}$CNMR and mass spectral analyses.

EXAMPLE 2

Preparation of 4-[(Z)-(2,3-Dihydro-3,3,4-trimethylbenzo[b]thien-5-yl)(dimethylamino)methylene]-1-methyl-2-pyrazolin-5-one S,S-dioxide

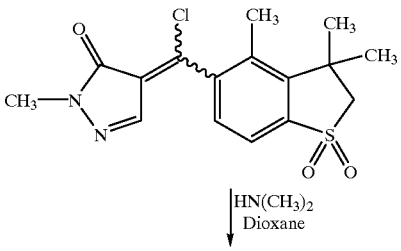

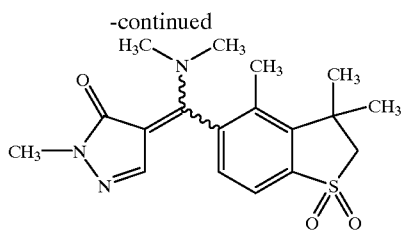

Dimethylamine gas is bubbled through a stirred solution of 4-[(Z)-chloro(2,3-dihydro-3,3,4-trimethylbenzo[b]thien-5-yl)methylene]-1-methyl-2-pyrazolin-5-one S,S-dioxide (0.100 g, 0.280 mmol) in dioxane at room temperature for two hours. The solution is concentrated in vacuo to give a residue. The residue is taken up in methylene chloride, washed successively with cold 10% aqueous sodium carbonate and brine, dried over anhydrous magnesium sulfate, and concentrated in vacuo to give a second residue. This residue is taken up in methylene chloride and chromatographed on silica gel using a gradient elution (methylene chloride/methanol: 100/0 to 98/2) to afford the title compound as a solid (0.064 g, 64%, mp 205–207° C.), identified by IR, $^1$HNMR, $^{13}$CNMR and mass spectral analyses.

EXAMPLE 3

Preparation of 4-[(Z)-(2,3-Dihydro-3,3,4-trimethylbenzo-[b]thien-5-yl)(p-methoxyphenoxy)methylene]-1-methyl-2-pyrazolin-5-one, S,S-dioxide

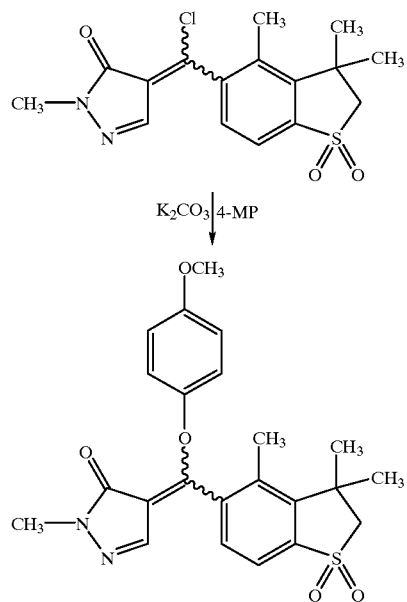

A mixture of 4-[(Z)-chloro(2,3-dihydro-3,3,4-trimethylbenzo[b]thien-5-yl)methylene]-1-methyl-2-pyrazolin-5-one S,S-dioxide (0.100 g, 28.4 mmol), 4-methoxyphenol (4-MP) (0.040 g, 32.2 mmol) and potassium carbonate (0.045 g, 32.6 mmol) in dry N,N-dimethylformamide is stirred at room temperature for 16 hr, diluted with cold water and extracted with methylene chloride. The combined organic extracts are washed with 10% aqueous sodium carbonate and brine, dried over anhydrous magnesium sulfate, and concentrated in vacuo to give a residue. The residue is chromatographed on silica gel with ethyl acetate-hexanes to afford the title compound as a light yellow semi-solid, 0.040g (32% yield) characterized by $^1$HNMR, $^{13}$CNMR and mass spectral analyses.

EXAMPLE 4

Preparation of 6-[(1-Ethyl-5-hydroxypyrazol-4-yl)thiocarbonyl]-5-methylthiochroman-4-one (E)-O-methyloxime, 1,1-dioxide

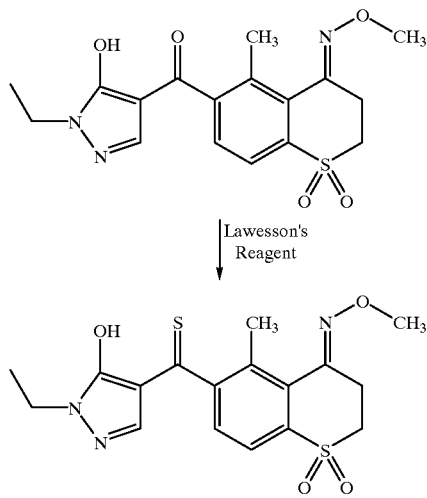

A stirred suspension of the 4-(O-methyloxime) of 6-[(1-ethyl-5-hydroxypyrazol-4-yl)carbonyl]-2,3-dihydro-5-methyl-4H-1-benzothiopyran-4-one, 1,1-dioxide (50.0 g, 0.132 mol) in dimethoxyethane, under nitrogen, is treated with Lawesson's Reagent (53.6 g, 0.132 mol), heated at 65–70° C. for a period of 15 h [during this period, additional Lawesson's Reagent is added (39.5 g, 0.098 mol)], cooled to room temperature and filtered. The filtrate is concentrated in vacuo to give a syrup. The syrup is diluted with diethyl ether, washed sequentially with water and brine, dried over sodium sulfate and concentrated in vacuo to give a second syrup. The second syrup is dissolved in methylene chloride and chromatographed on silica gel using a gradient elution (methylene chloride/diethyl ether: 100/0 to 90/10) to give the title compound as a golden yellow solid, mp 92°–97° C., 24.1 g, (46.1% yield), identified by IR, $^1$HNMR, $^{13}$CNMR and MS analyses. Quantitative NMR analysis indicates a product purity of 97.7% with the ratio of oxime isomers (E/Z: 95/5) unchanged from the ratio found in the starting material.

EXAMPLE 5

Preparation of 2,3-Dihydro-3,3,4-trimethylbenzo[b]thien-5-yl 5-hydroxy-1-methylpyrazol-4-yl thione 1,1-dioxide

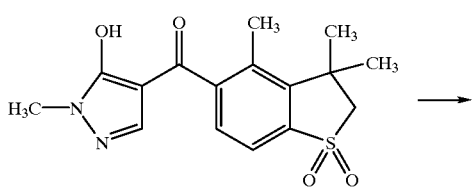

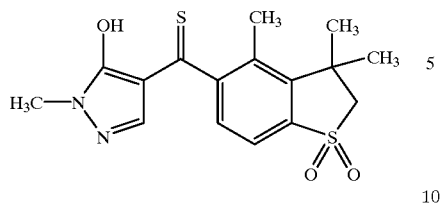

Using essentially the same procedure as described above in example 4 and employing on 2,3-dihydro-5-[(5-hydroxy-1-methylpyrazol-4-yl)carbonyl]-3,3,4-trimethyl-benzo[b]thiophene 1,1-dioxide, affords the title product as a light yellow powder, mp 214–216° C., characterized by IR, $^1$HNMR, $^{13}$CNMR and mass spectral analyses.

EXAMPLE 6

Preparation of 4-Methoximino-5-methyl-6-(1-ethyl-5-hydroxypyrazol-4-yl)thiocarbonylthiochroman-1,1-dioxide, zinc (+2) chelate

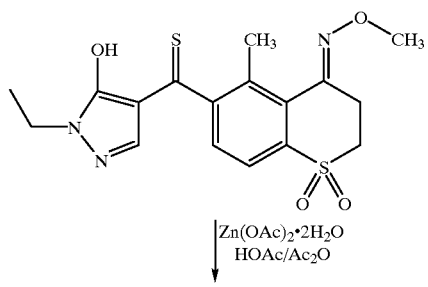

A mixture of finely ground zinc acetate dihydrate (0.233 g, 1.067 mmol) in glacial acetic acid is treated with acetic anhydride (0.217 g, 2.13 mmol) and heated to reflux briefly to give a suspension. This suspension is added, while hot, to a solution of 6-[(1-ethyl-5-hydroxypyrazol-4-yl)thiocarbonyl]-5-methylthiochroman-4-one (E)-O-methyloxime, 1,1-dioxide (0.84 g, 2.13 mmol) in glacial acetic acid. The reaction mixture is heated to reflux for five minutes, cooled and filtered. The filtercake is washed with acetic acid and air-dried to afford the title compound as a bright orange yellow solid, 0.25 g (27% yield), mp>255° C., identified by IR, $^1$HNMR, $^{13}$CNMR and mass spectral analyses.

EXAMPLE 7

Preparation of 4,4'-[(Z,Z)-Dithiobis[(2,3-dihydro-3,3,4-trimethylbenzo[b]thien-5-yl)methylidyne]]bis[1-methyl-2-pyrazolin-5-one] S,S,S',S',-tetraoxide, 80:20 mixture with 4,4'-[(E,Z)-dithiobis[(2,3-dihydro-3,3,4-trimethyl-benzo[b]thien-5-yl)methylidyne]]bis[1-methyl-2-pyrazolin-5-one] S,S,S',S'-tetraoxide

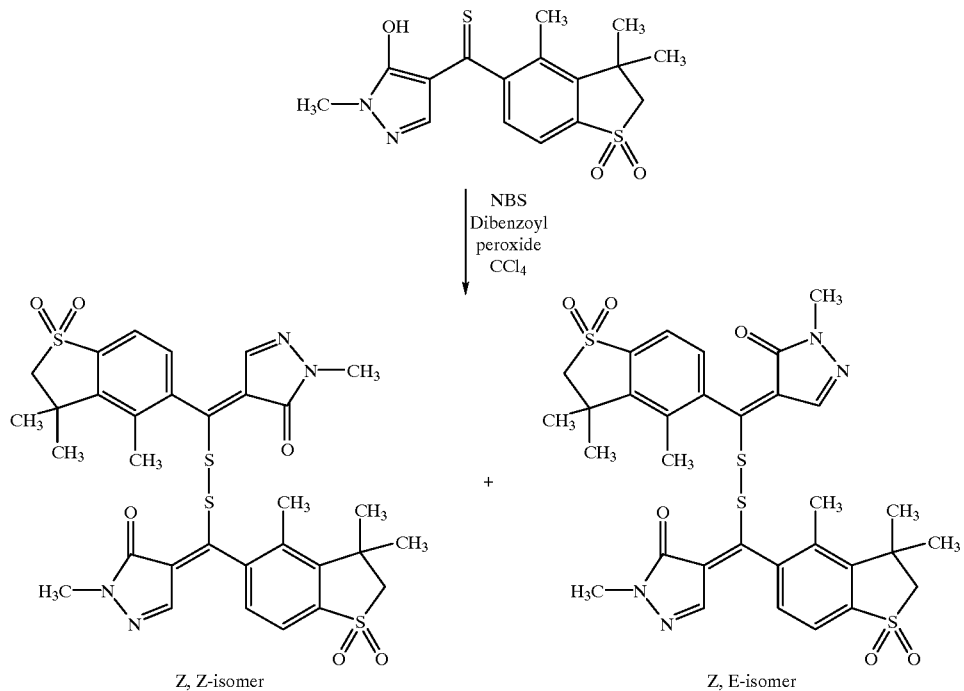

A mixture of 2,3-dihydro-3,3,4-trimethylbenzo[b]thien-5-yl 5-hydroxy-1-methylpyrazol-4-yl thione 1,1-dioxide(0.15 g, 0.428 mmol), N-bromosuccinimide (NBS) (0.0914 g, 0.514 mmol), and dibenzoyl peroxide (0.020 g, 0.041 mmol) in carbon tetrachloride is refluxed for 15 minutes, cooled to room temperature, washed with water and brine, dried over anhydrous sodium sulfate and concentrated in vacuo to give a syrup. The residual yellow-orange syrup is chromatographed on silica gel using a gradient elution (methylene chloride/diethyl ether: 100/0 to 90/10) to afford the title product mixture as a light yellow syrup, 0.11 g (73% yield), identified by NMR analysis to be of an 80:20 mixture of the (Z,Z):(Z:E) isomers.

EXAMPLE 8

Preparation of 1-Ethyl-4-[(E)-(5-methyl-4-oxothiochroman-6-yl)(propylthio)methylene]-2-pyrazolin-5-one 4'-[(E)-O-methyloxime], S,S-dioxide (Example 8a) and 1-Ethyl-4-[(Z)-(5-methyl-4-oxothiochroman-6-yl)(propythio)methylene]-2-pyrazolin-5-one 4'-[(E)-O-methyloxime], S,S-dioxide (Example 8b)

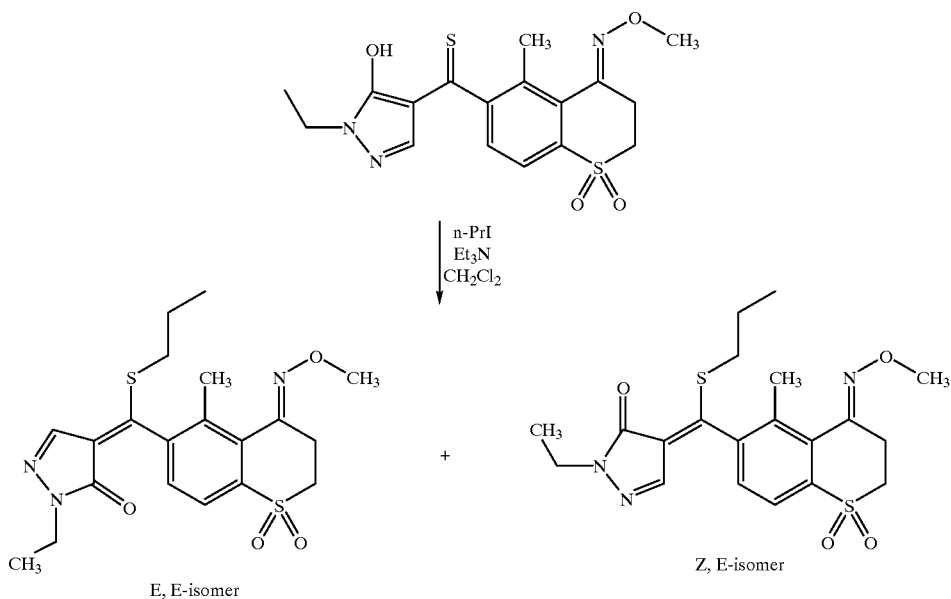

E, E-isomer

Z, E-isomer

A solution of 6-[(1-ethyl-5-hydroxypyrazol-4-yl)thiocarbonyl]-5-methylthiochroman-4-one (E)-O-methyloxime, 1,1-dioxide (1.00 g, 2.54 mmol) and triethylamine (Et$_3$N) (0.27 g, 2.67 mmol) in methylene chloride at −5° C. is treated with n-propyl iodide (0.45 g, 2.67 mmol), stirred overnight at room temperature, poured onto ice, acidified with 10% hydrochloric acid and diluted with methylene chloride. The phases are separated. The organic phase is washed sequentially with water and brine, dried over anhydrous magnesium sulfate and concentrated in vacuo to afford a residue. Gradient elution chromatography on silica gel (methylene chloride/diethyl ether: 100/0 to 90/10) affords two yellow solid fractions. Recrystallization of each from methylene chloride/hexanes afforded the title product E,E-isomer (designated 8a), 0.19 g(17% Yield) mp 173–176° C. and the title product Z,E-isomer (designated 8b), 0.41 g(37% yield) mp 195–196° C. Each isomeric product is characterized by IR, $^1$HNMR, $^{13}$CNMR and mass spectral analyses.

EXAMPLE 9

Preparation of 4-{(Z)-(2,3-Dihydro-3,3,4-trimethylbenzo-[b]thien-5-yl)(propylthio)methylene]-1-methyl-2-pyrazolin-5-one S,S-dioxide

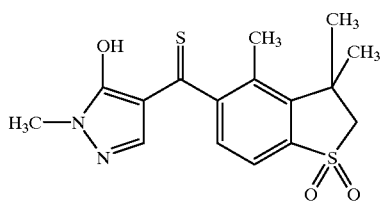

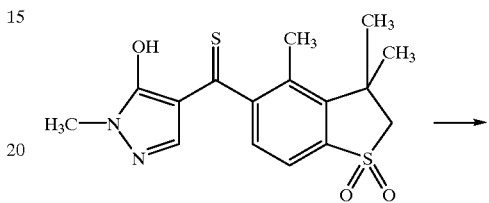

-continued

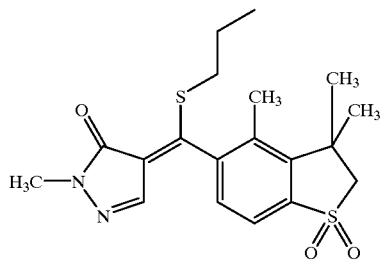

Following essentially the same procedure described above in Example 8 and employing 2,3-dihydro-3,3,4-trimethylbenzo[b]thien-5-yl 5-hydroxy-1-methylpyrazol-4-yl thione 1,1-dioxide affords the title product, mp 185.5–187° C. (10% yield), identified by IR, $^1$HNMR, $^{13}$CNMR and mass spectral analyses.

EXAMPLE 10

Prepration of Substituted Methylene Pyrazolinone Compounds

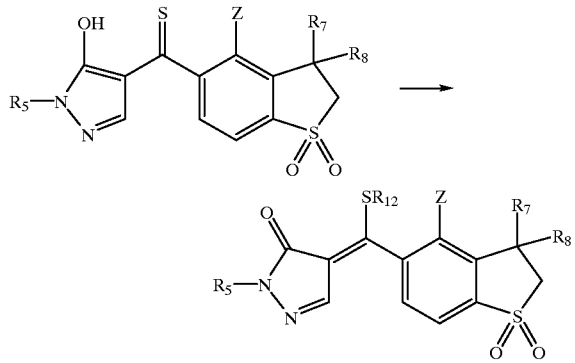

Using essentially the same procedures described hereinabove and employing the appropriate substrate and alkylating agent the following compounds are obtained.

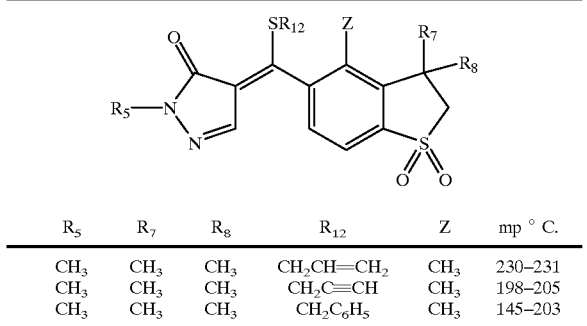

| $R_5$ | $R_7$ | $R_8$ | $R_{12}$ | Z | mp °C. |
|---|---|---|---|---|---|
| $CH_3$ | $CH_3$ | $CH_3$ | $CH_2CH=CH_2$ | $CH_3$ | 230–231 |
| $CH_3$ | $CH_3$ | $CH_3$ | $CH_2C\equiv CH$ | $CH_3$ | 198–205 |
| $CH_3$ | $CH_3$ | $CH_3$ | $CH_2C_6H_5$ | $CH_3$ | 145–203 |

EXAMPLE 11

Preparation of 1-Ethyl-4-[(E)-(5-methyl-4-oxothiochroman-6-yl) (propylsulfonyl)methylene]-2-pyrazolin-5-one 4'-[(E)-O-methyloxime, S,S-dioxide, 62:38 mixture with 1-ethyl-4-[(Z)-(5-methyl-4-oxothiochroman-6-yl) (propylsulfonyl)methylene]-2-pyrazolin-5-one 4'-[(E)-O-methyloxime], S,S-dioxide

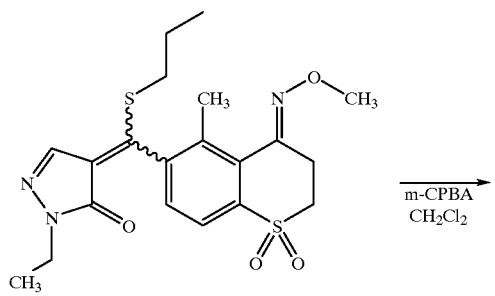

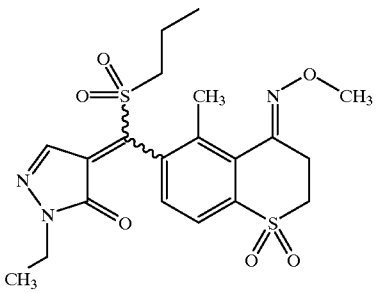

A solution of 1-ethyl-4-[(E)-(5-methyl-4-oxothiochroman-6-yl) (propylthio)methylene]-2-pyrazolin-5-one 4'-[(E)-O-methyloxime], S,S-dioxide and 1-ethyl-4-[(Z)-(5-methyl-4-oxothiochroman-6-yl) (propylthio)methylene]-2-pyrazolin-5-one 4'-[(E)-O-methyloxime], S,S-dioxide (0.20 g, 0.469 mmol) in methylene chloride at room temperature is treated dropwise with a solution of 57% m-chloroperbenzoic acid (m-CPBA) (0.24 g, 1.38 mmol) in methylene chloride, stirred for 4.5 hours, cooled to room temperature, washed sequentially with 10% aqueous sodium bicarbonate, water and brine, dried over anhydrous magnesium sulfate and concentrated in vacuo to afford a residue. The residue is chromatographed on silica gel using methylene chloride/ether to give the title product as a 62:38 E:Z isomer mixture, mp 84–89° C., 0.16 g, (74% yield), identified by IR, $^1$HNMR, $^{13}$CNMR and mass spectral analyses.

EXAMPLE 12

Postemergence Herbicidal Evaluation Of Test Compounds

The postemergence herbicidal activity of the compounds of the present invention is evaluated by the following tests. Seedling plants are grown in jiffy flats for about two weeks. The test compounds are dispersed in 80/20 (v/v) acetone/water mixtures containing 1.0% SUN-IT®II, a methylated seed oil, in sufficient quantities to provide the equivalent of about 0.006 kg/ha to 0.800 kg/ha of active compound when applied to the plants through a spray nozzle operating at 40 psi for a predetermined time. After spraying, the plants are placed on greenhouse benches and are cared for in accordance with conventional greenhouse procedures. Approximately two to three weeks after treatment, the seedling plants are examined and rated according to the rating system set forth below. Where more than one test is involved for a given compound, the data are averaged. The results are shown in Table I.

| HERBICIDE RATING SCALE | |
|---|---|
| Rating | % Control Compared to Check |
| 9 | 100 |
| 8 | 91–99 |
| 7 | 80–90 |
| 6 | 65–79 |
| 5 | 45–64 |
| 4 | 30–44 |
| 3 | 16–29 |
| 2 | 6–15 |
| 1 | 1–5 |
| 0 | 0 |

| Column Heading | Common Name | Scientific Name |
|---|---|---|
| | PLANT SPECIES | |
| ABUTH | Velvetleaf | *Abutilon theophrasti*, Medic. |
| AMBEL | Ragweed | *Ambrosia artemisifolia*, L. |
| CHEAL | Lambsquarters | *Chenopodium album*, L. |
| IPOSS | Morningglory spp. | *Ipomoea* spp. |
| ECHCG | Barnyardgrass | *Echinochloa crus-galli*, (L.) Beau |
| PANDI | Panicum, Fall | *Panicum dichotomiflorum*, Michx |
| SETVI | Foxtail, Green | *Setaria viridis*, (L.) Beau |
| GOSHI | Cotton | *Gossypium hirsutum*, L. |
| ORYSAT | Rice, Tebonnet | *Oryza sativa*, (L.) Tebonnet |
| ZEAMX | Corn, Field | *Zea mays*, L. (Sammel-Bezeichnung) |

EXAMPLE 13

Preemergence Herbicidal Evaluation Of Test Compounds

The preemergence herbicidal activity of the test compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.0125 kg/ha to 0.800 kg/ha of test compound per cup. The treated cups are then placed on greenhouse benches, watered and cared for in accordance with conventional greenhouse procedures. Approximately two to four weeks after treatment, the tests are terminated and each cup is examined and rated according to the rating system provided in Example 12. When more than one test is performed for a given compound, the data are averaged. The results are shown in Table II.

TABLE I

Postemergence Herbicidal Evaluation

| Ex. No. | Rate (kg/ha) | ABUTH | AMBEL | CHEAL | IPOSS | ECHCG | PANDI | SETVI | GOSHI | ORYSAT | ZEAMX |
|---|---|---|---|---|---|---|---|---|---|---|---|
| 2 | 0.1000 | 0.0 | 0.0 | 0.0 | | 0.0 | | 0.0 | | | 0.0 |
| 2 | 0.0500 | 0.0 | 0.0 | 0.0 | | 0.0 | | 0.0 | | | 0.0 |
| 2 | 0.0250 | 0.0 | 0.0 | 0.0 | | 0.0 | | 0.0 | | | 0.0 |
| 2 | 0.0125 | 0.0 | 0.0 | 0.0 | | 0.0 | | 0.0 | | | 0.0 |
| 3 | 0.1000 | 7.0 | 7.0 | 9.0 | | 6.0 | | 7.0 | | | 2.0 |
| 3 | 0.0500 | 7.0 | 7.0 | 8.0 | | 4.0 | | 5.0 | | | 0.0 |
| 3 | 0.0250 | 4.0 | 4.0 | 6.0 | | 3.0 | | 3.0 | | | 0.0 |
| 3 | 0.0125 | 2.0 | 2.0 | 6.0 | | 2.0 | | 1.0 | | | 0.0 |
| 7 | 0.1000 | 7.0 | 9.0 | | 2.0 | 9.0 | 9.0 | 9.0 | | 7.0 | 2.0 |
| 7 | 0.0500 | 5.0 | 9.0 | | 2.0 | 8.0 | 7.0 | 9.0 | | 7.0 | 0.0 |
| 7 | 0.0250 | 4.0 | 7.0 | | 1.0 | 7.0 | 3.0 | 7.0 | | 6.0 | 0.0 |
| 7 | 0.0125 | 3.0 | 4.0 | | 1.0 | 7.0 | 5.0 | 7.0 | | 3.5 | 0.0 |
| 8a | 0.8000 | 6.0 | 8.0 | 9.0 | 4.0 | 9.0 | 9.0 | 9.0 | 6.0 | 5.0 | 0.5 |
| 8a | 0.4000 | 8.0 | 7.0 | 9.0 | 2.0 | 9.0 | 6.0 | 8.0 | 3.0 | 5.0 | 0.0 |
| 8a | 0.2000 | 2.0 | 6.0 | 9.0 | 0.0 | 8.0 | 7.0 | 5.0 | 0.0 | 1.5 | 0.0 |
| 8a | 0.1000 | 1.0 | 3.0 | 9.0 | 0.0 | 8.0 | 6.0 | 4.0 | 0.0 | 0.7 | 0.0 |
| 8a | 0.0500 | 0.0 | 2.0 | 7.0 | 0.0 | 8.0 | 3.0 | 1.0 | 0.0 | 0.0 | 0.0 |
| 8b | 0.8000 | 6.0 | 7.0 | 9.0 | 0.0 | 9.0 | 6.0 | 9.0 | 4.5 | 3.5 | 0.0 |
| 8b | 0.4000 | 5.0 | 7.0 | 9.0 | 0.0 | 9.0 | 7.0 | 9.0 | 4.0 | 1.5 | 0.0 |
| 8b | 0.2000 | 5.0 | 7.0 | 8.0 | 0.0 | 8.0 | 7.0 | 4.0 | 0.0 | 3.5 | 0.0 |
| 8b | 0.1000 | 0.0 | 5.0 | 8.0 | 0.0 | 8.0 | 6.0 | 3.5 | 0.0 | 1.7 | 0.0 |
| 8b | 0.0500 | 1.0 | 0.0 | 7.0 | 0.0 | 6.5 | 2.0 | 3.5 | 0.0 | 1.0 | 0.0 |
| 10 | 0.8000 | 7.0 | 9.0 | 9.0 | 5.0 | 8.0 | 8.0 | 9.0 | 6.5 | 7.0 | 6.0 |
| 10 | 0.4000 | 8.0 | 8.0 | 9.0 | 5.0 | 9.0 | 8.0 | 9.0 | 6.5 | 7.0 | 6.0 |
| 10 | 0.2000 | 8.0 | 8.0 | 9.0 | 3.0 | 8.0 | 8.0 | 9.0 | 6.5 | 7.5 | 3.5 |
| 10 | 0.1000 | 6.0 | 8.0 | 9.0 | 3.0 | 9.0 | 7.0 | 9.0 | 5.0 | 7.0 | 0.5 |
| 10 | 0.0500 | 6.0 | 8.0 | 9.0 | 5.0 | 8.0 | 8.0 | 9.0 | 5.0 | 5.5 | 0.0 |

TABLE II

Preemergence Herbicidal Evaluation

| Ex. No. | Rate (kg/ha) | ABUTH | AMBEL | CHEAL | IPOSS | ECHCG | PANDI | SETVI | GOSHI | ORYSAT | ZEAMX |
|---|---|---|---|---|---|---|---|---|---|---|---|
| 6 | 0.8000 | 9.0 | 9.0 | 9.0 | 5.0 | 8.0 | 8.0 | 9.0 | 7.0 | 9.0 | 0.0 |
| 6 | 0.4000 | 9.0 | 9.0 | 9.0 | 5.0 | 9.0 | 8.0 | 9.0 | 8.0 | 9.0 | 1.0 |
| 6 | 0.2000 | 9.0 | 9.0 | 9.0 | 6.0 | 9.0 | 9.0 | 9.0 | 6.0 | 9.0 | 0.0 |
| 6 | 0.1000 | 9.0 | 8.0 | 9.0 | 3.0 | 9.0 | 9.0 | 7.0 | 1.0 | 7.0 | 0.0 |
| 6 | 0.0500 | 9.0 | 7.0 | 9.0 | 1.0 | 3.0 | 6.0 | 4.0 | 0.0 | 4.0 | 0.0 |
| 8a | 0.8000 | 6.0 | 6.0 | 9.0 | 2.0 | 2.0 | 8.0 | 5.0 | 2.0 | 3.0 | 0.0 |
| 8a | 0.4000 | 2.0 | 3.0 | 9.0 | 0.0 | 0.0 | 5.0 | 4.0 | 0.0 | 0.0 | 0.0 |
| 8b | 0.8000 | 9.0 | 6.0 | 9.0 | 0.0 | 0.0 | 7.0 | 3.0 | 0.0 | 0.0 | 0.0 |
| 8b | 0.4000 | 0.0 | 3.0 | 7.0 | 0.0 | 0.0 | 7.0 | 0.0 | 0.0 | 0.0 | 0.0 |
| 8b | 0.2000 | 0.0 | 0.0 | 6.0 | 0.0 | 0.0 | 2.0 | 3.0 | 0.0 | 0.0 | 0.0 |
| 10 | 0.8000 | 9.0 | 9.0 | 9.0 | 7.0 | 9.0 | 8.0 | 9.0 | 7.0 | 8.0 | 6.0 |
| 10 | 0.4000 | 9.0 | 9.0 | 8.0 | 3.0 | 8.0 | 8.0 | 9.0 |  | 6.0 | 0.0 |
| 10 | 0.2000 | 8.0 | 9.0 | 9.0 | 4.0 | 7.0 | 8.0 | 9.0 | 6.0 | 7.0 | 0.0 |
| 10 | 0.1000 | 9.0 | 9.0 | 9.0 | 7.0 | 8.0 | 7.0 | 9.0 | 5.0 | 8.0 | 1.0 |
| 10 | 0.0500 | 9.0 | 6.0 | 9.0 | 2.0 | 6.0 | 7.0 | 8.0 | 1.0 | 6.0 | 0.0 |

What is claimed is:

1. A compound of formula I

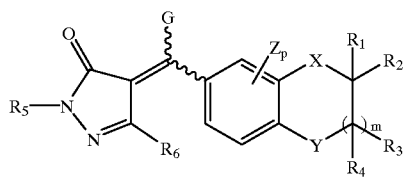

(I)

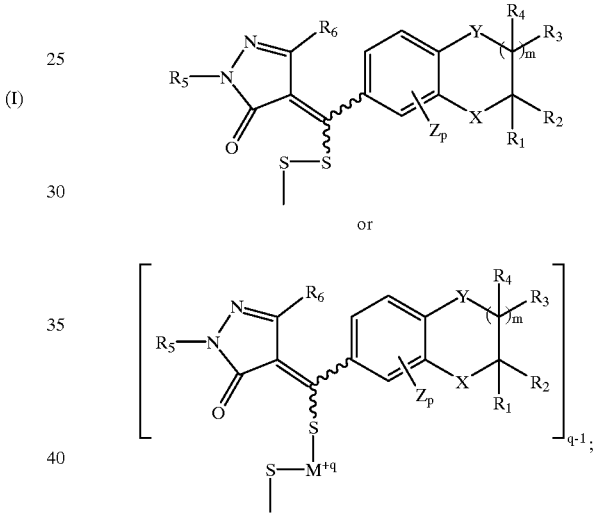

or wherein m is zero or 1;

$R_1, R_2, R_3$ and $R_4$ are each independently H, $C_1$–$C_4$ alkyl, $C_1$–$C_4$ haloalkyl or $C_2$–$C_4$ alkoxyalkyl;

$R_5$ is $C_1$–$C_3$ alkyl, $C_3$–$C_4$ alkenyl or $C_3$–$C_4$ haloalkenyl;

$R_6$ is H, halogen, CN, $C_1$–$C_4$ alkyl, $C_2$–$C_4$ alkenyl, $C_1$–$C_4$ alkoxyalkyl or $C_1$–$C_4$ alkoxycarbonyl;

X is $CR_7R_8$, $CHOR_9$, $C=NNR_{16}R_{17}$, $C=NOR_{10}$, $C=O$ or $C(OR_9)_2$;

$R_7$ is H, $C_1$–$C_4$ alkyl or $C_1$–$C_4$ haloalkyl;

$R_8$ is H, $C_1$–$C_4$ alkyl, $C_2$–$C_4$ alkynyl or $C_1$–$C_4$ alkoxyalkyl;

$R_9$ and $R_{10}$ are each, independently H or $C_1$–$C_6$ alkyl optionally substituted with one or more $C_2$–$C_6$ alkenyl, $C_2$–$C_6$ haloalkyl or $C_3$–$C_6$ cycloalkyl groups;

Y is O, S, SO or $SO_2$;

Z is H, halogen, $C_1$–$C_4$ alkyl, $C_1$–$C_4$ haloalkyl, $C_2$–$C_4$ alkoxyalkyl, $C_1$–$C_4$ alkoxy or $C_1$–$C_4$ haloalkoxy;

p is an integer of 1,2 or 3;

G is $OR_{11}$, $OCH_2COR_{11}$, $OCN_2CSR_{11}$, $SCH_2CSR_{11}$, $OCOR_{11}$, $SCOR_{11}$, $OCSR_{11}$, $SCSR_{11}$, $S(O)_nR_{12}$, $NR_{13}R_{14}$, $P(O)(OR_{15})_2$, halogen, CN, SCN, n is zero, 1 or 2;

$R_{11}$ and $R_{12}$ are each independently $C_1$–$C_6$ alkyl, $C_1$–$C_6$ halo alkyl, $C_2$–$C_6$ alkenyl, $C_2$–$C_6$ haloalkenyl, $C_2$–$C_6$ haloalkynyl, $C_1$–$C_6$ alkoxyalky, benzyl optionally substituted with one to three halogen, $C_1$–$C_6$ alkyl, $C_1$–$C_6$ alkoxy, or $C_1$–$C_6$ haloalkyl groups, or phenyl optionally substituted with one to three halogen, $C_1$–$C_6$ alkyl, $C_1$–$C_6$ alkoxy, or $C_1$–$C_6$ haloalkyl groups;

$R_{13}$ and $R_{14}$ are each independently hydrogen, $C_1$–$C_6$ alkyl, $C_3$–$C_6$ alkenyl, $C_3$–$C_6$ alkynyl, or $R_{13}$ and $R_{14}$ maybe taken together with the atoms to which they are attached to represent a four -to seven=membered ring optionally interrupted by oxygen, sulfur or nitrogen and optionally substituted with one to three halogen or $C_1$–$C_6$ alkyl groups; $R_{15}$ is $C_{1-C6}$ alkyl; $R_{16}$ is H or $C_1$–$C_6$ alkyl;

$R_{17}$ is H, $C_{1-C6}$ alkyl, $C_1$–$C_6$ haloalkyl, $C_2$–$C_6$ alkoxycarbonyl, $C_2$–$C_6$ alkylcarbonyl, $COR_{18}$ or phenyl optionally substituted with one to three $C_1$–$C_3$ alkyl, halogen, CN or $NO_2$ groups, or $R_{16}$ and $R_{17}$ may be taken together to represent =$C(C_1-C_3$ alkyl$)_2$;

$R_{18}$ is phenyl optionally substituted with one to three $C_1-C_3$ alkyl, halogen, CN or $NO_2$ groups;

M is a transition metal or an alkaline-earth metal; and q is an integer of 1,2 or 3; or the geometric or optically active isomers thereof.

2. The compound according to claim 1 wherein $R_1$, $R_2$, $R_3$ and $R_4$ are each independently H or $C_{1-C4}$ alkyl;

$R_5$ is $C_{1-C3}$ alkyl;

$R_6$ is H or $C_{1-C4}$ alkyl;

X is $CR_7R_8$ or $C=NOR_{10}$;

$R_7$ and $R_8$ are each independently H or $C_1-C_4$ alkyl;

$R_{10}$ is H or $C_{1-C6}$ alkyl;

Y is $SO_2$;

Z is H, halogen or $C_{1-C4}$ alkyl;

G is $OR_{11}$, $S(O)_nR_{12}$,

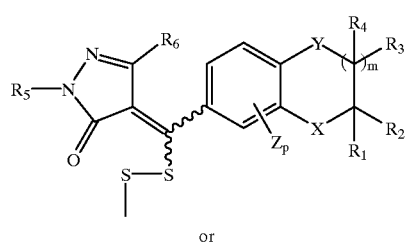

or

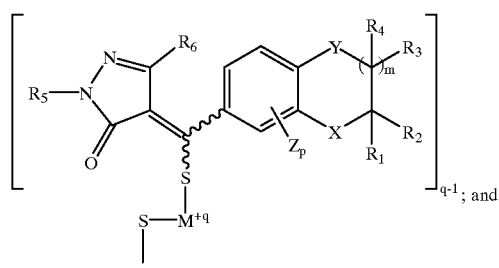

$R_{11}$ and $R_{12}$ are each independently $C_{1-C6}$ alkyl or phenyl optionally substituted with one to three halogen, $C_{1-C6}$ alkyl, $C_{1-C6}$ alkoxy, or $C_{1-C6}$ haloalkyl groups.

3. The compound according to claim 2 wherein m is zero;

$R_1$ and $R_2$ are H;

$R_5$ is $C_{1-C3}$ alkyl;

$R_6$ is H;

X is $CR_7R_8$;

$R_7$ and $R_8$ are each independently $C_{1-C4}$ alkyl;

Z is $C_{1-C4}$ alkyl;

p is 1;

G is $OR_{11}$, $S(O)_nR_{12}$,

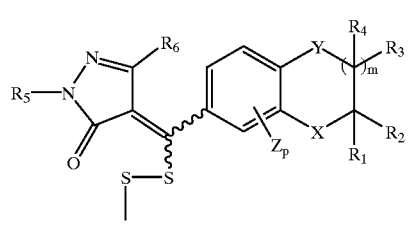

or

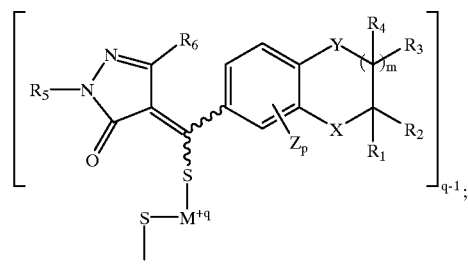

n is zero or 2;

$R_{11}$ is phenyl optionally substituted with one to three halogen, $C_{1-C2}$ alkyl, $C_{1-C3}$ alkoxy, or $C_{1-C3}$ haloalkyl groups; and $R_{12}$ is $C_{1-C6}$ alkyl.

4. The compound according to claim 2 wherein m is 1;

$R_1$, $R_2$, $R_3$ and $R_4$ are H;

$R_5$ is $C_{1-C3}$ alkyl;

$R_6$ is H;

X is $C=NOR_{10}$;

$R_{10}$ is $C_{1-C6}$ alkyl;

Z is $C_{1-C4}$ alkyl;

p is 1;

G is $OR_{11}$, $S(O)_nR_{12}$,

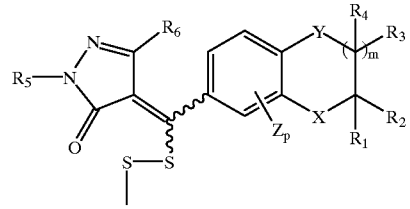

or

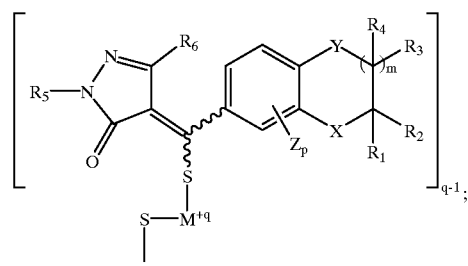

n is zero or 2;

$R_{11}$ is phenyl optionally substituted with one to three halogen, $C_{1-C2}$ alkyl, $C_{1-C3}$ alkoxy, or $C_{1-C3}$ haloalkyl groups; and $R_{12}$ is $C_{1-C6}$ alkyl.

5. The compound according to claim 1 selected from the group consisting of:

1-ethyl-4-[(E)-(5-methyl-4-oxothiochroman-6-yl) (propylthio)methylene]-2-pyrazolin-5-one 4'-[(E)-O-methyloxime], S,S-dioxide;

1-ethyl-4-[(Z)-(5-methyl-4-oxothiochroman-6-yl) (propylthio)methylene]-2-pyrazolin-5-one 4'-[(E)-O-methyloxime], S,S-dioxide;

1-ethyl-4-[(E)-(5-methyl-4-oxothiochroman-6-yl)
(propylsulfonyl)methylene]-2-pyrazolin-5-one 4'-[(E)-
O-methyloxime], S,S-dioxide;

1-ethyl-4-[(Z)-(5-methyl-4-oxothiochroman-6-yl)
(propylsulfonyl)methylene]-2-pyrazolin-5-one 4'-[(E)-
O-methyloxime}, S,S-dioxide;

4,4'-[(Z,Z)-dithiobis[(2,3-dihydro-3,3,4-trimethylbenzo
[b]thien-5-yl)methylidyne]]bis]1-methyl-2-pyrazolin-
5-one] S,S,S',S'-tetraoxide;

4,4'-[(E,Z)-dithiobis[(2,3-dihydro-3,3,4-trimethylbenzo
[b]thien-5-yl)methylidyne]]bis[1-methyl-2-pyrazolin-
5-one] S,S,S',S'-tetraoxide;

4-[(Z)-(2,3-dihydro-3,3,4-trimethylbenzo[b]thien-5-yl)
(propylthio)methylene]-1-methyl-2-pyrazolin-5-one
S,S-dioxide;

4-{(Z)-(2,3-dihydro-3,3,4-trimethylbenzo[b]thien-5-yl)
[(m-trifluoromethyl)anilino]methylene}-1-methyl-2-
pyrazolin-5-one S,S-dioxide; and 4-(Z)-(2,3-dihydro-3,3,4-trimethylbenzo[b]thien-5-yl)(p-
methoxyphenoxy)methylene]-1-methyl-2-pyrazolin-5-
one S,S-dioxide.

6. A method for the control of undesirable monocotyledenous and dicotyledenous plants which comprises applying to the foliage of said plants or to the soil or water containing seeds or other propagating organs thereof a herbicidally effective amount of a compound of formula I

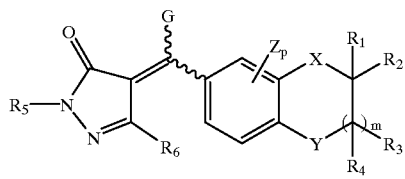

(I)

wherein $R_1$ $R_2$, $R_3$, $R_4$, $R_5$, $R_6$, G, X, Y, Z, m and p are as defined in claim 1.

7. The method according to claim 6 having a formula I compound wherein $R_1$, $R_2$, $R_3$ and $R_4$ are each independently H, or $C_1$–$C_4$ alkyl;

$R_5$ is $C_1$–$C_3$ alkyl;

$R_6$ is H, or $C_1$–$C_4$ alkyl;

X is $CR_7R_8$ or C=$NOR_{10}$;

$R_7$ and $R_8$ are each independently H or $C_1$–$C_4$ alkyl;

$R_{10}$ is H or $C_1$–$C_6$ alkyl;

Y is $SO_2$;

Z is H, halogen, or $C_1$–$C_4$ alkyl;

G is $OR_{11}$, $SO_nR_{12}$,

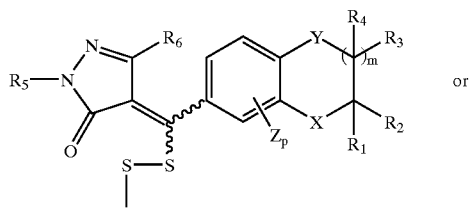

or

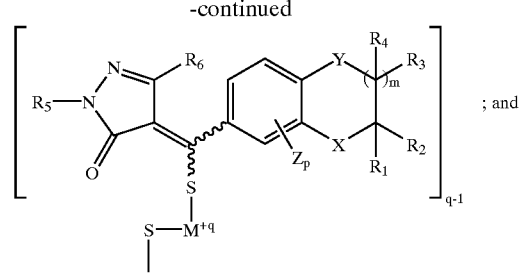

; and $R_{11}$ and $R_{12}$ are each independently $C_1$–$C_6$ alkyl or phenyl optionally substituted with one to three halogen, $C_1$–$C_6$ alkyl, $C_1$–$C_6$ alkoxy or $C_1$–$C_6$ haloalkyl groups.

8. The method according to claim 7 having a formula I compound wherein m is zero;

$R_1$ and $R_2$ are H;

$R_5$ is $C_1$–$C_3$ alkyl;

$R_6$ is H;

X is $CR_7R_8$;

$R_7$ and $R_8$ are each interdependently $C_1$–$C_4$ alkyl;

Z is $C_1$–$C_4$ alkyl;

p is 1;

G is $OR_{11}$, $S(O)_nR_{12}$,

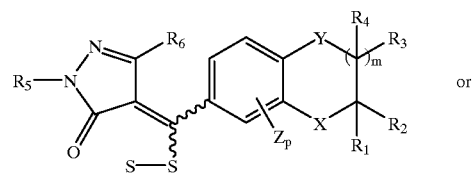

or

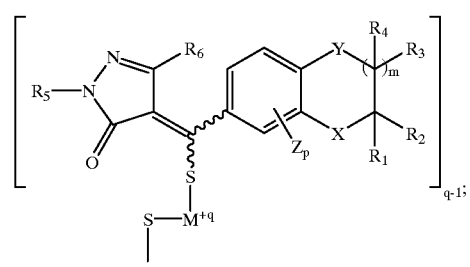

n is zero or 2;

$R_{11}$ is phenyl optionally substituted with one to three halogen, $C_1$–$C_2$ alkyl, $C_1$–$C_3$ alkoxy or $C_1$–$C_3$ haloalkyl groups; and $R_{12}$ is $C_1$–$C_6$ alkyl.

9. The method according to claim 7 having a formula I compound wherein m is 1;

$R_1$, $R_2$, $R_3$ and $R_4$ are H;

$R_5$ is $C_1$–$C_3$ alkyl;

$R_6$ is H;

X is C=$NOR_{10}$;

$R_{10}$ is $C_1$–$C_6$ alkyl;

Z is $C_1$–$C_4$ alkyl;

p is 1;

G is $OR_{11}$, $S(O)_nR_{12}$, n is zero or 2;

$R_{11}$ is phenyl optionally substituted with one to three halogen, $C_1$–$C_2$ alkyl, $C_1$–$C_3$ alkoxy or $C_1$–$C_3$ haloalkyl groups; and $R_{12}$ is $C_1$–$C_6$ alkyl.

10. The method according to claim 6 wherein the compound of formula I is selected from the group consisting of:

1-ethyl-4-[(E)-(5-methyl-4-oxothiochroman-6-yl) (propylthio)methylene]-2-pyrazolin-5-one 4'-[(E)-O-methyloxime], S,S-dioxide;

1-ethyl-4-[(Z)-(5-methyl-4-oxothiochroman-6-yl) (propylthio)methylene]-2-pyrazolin-5-one 4'-[(E)-O-methyloxime], S,S-dioxide;

1-ethyl-4-[(E)-(5-methyl-4-oxothiochroman-6-yl) (propylsulfonyl)methylene]-2-pyrazolin-5-one 4'-[(E)-O-methyloxime], S,S-dioxide;

1-ethyl-4-[(Z)-(5-methyl-4-oxothiochroman-6-yl) (propylsulfonyl)methylene]-2-pyrazolin-5-one 4'-[(E)-O-methyloxime}, S,S-dioxide;

4,4-[(Z,Z)-dithiobis[(2,3-dihydro-3,3,4-trimethylbenzo [b]thien-5-yl)methylidyne]]bis]1-methyl-2-pyrazolin-5-one] S,S,S',S'-tetraoxide;

4,4'-[(E,Z)-dithiobis[(2,3-dihydro-3,3,4-trimethylbenzo [b]thien-5-yl)methylidyne]]bis[1-methyl-2-pyrazolin-5-one] S,S,S',S'-tetraoxide;

4-[(Z)-(2,3-dihydro-3,3,4-trimethylbenzo[b]thien-5-yl) (propylthio)methylene]-1-methyl-2-pyrazolin-5-one S,S-dioxide;

4-{(Z)-(2,3-dihydro-3,3,4-trimethylbenzo[b]thien-5-yl) [(m-trifluoromethyl)anilino]methylene}-1-methyl-2-pyrazolin-5-one S,S-dioxide; and 4-[(Z)-(2,3-dihydro-3,3,4-trimethylbenzo[b]thien-5-yl) (p-methoxyphenoxy)methylene]-1-methyl-2-pyrazolin-5-one S,S-dioxide.

11. The method according to claim 6 wherein said undesirable plants are in the presence of a crop plant, crop seed or other crop propagating organ.

12. The method according to claim 11 wherein said crop is a cereal crop.

13. The method according to claim 12 wherein the cereal crop is corn or rice.

14. The method according to claim 6 wherein said formula I compound is applied at a rate of about 0.001 kg/ha to 1.0 kg/ha.

15. A herbicidal composition which comprises an inert solid or liquid carrier and a herbicidally effective amount of a compound of formula I (I)

wherein $R_1$, $R_2$, $R_3$, $R_4$, $R_5$, $R_6$, G, X, Y, Z, m and p are as defined in claim 1.

16. The composition according to claim 15 wherein $R_1$, $R_2$, $R_3$ and $R_4$ are each independently H or $C_1$-$C_4$ alkyl;

$R_5$ is $C_1$-$C_3$ alkyl;

$R_6$ is H, or $C_1$-$C_4$ alkyl;

X is $CR_7R_8$ or C=$NOR_{10}$;

$R_7$ and $R_8$ are each independently H or $C_1$-$C_4$ alkyl;

$R_{10}$ is H or $C_1$-$C_6$ alkyl;

Y is $SO_2$;

Z is H, halogen or $C_1$-$C_4$ alkyl;

G is $OR_{11}$, $SO_nR_{12}$, $R_{11}$ and $R_{12}$ are each independently $C_1$-$C_6$ alkylor phenyl optionally substituted with one to three halogen, $C_1$-$C_6$ alkyl $C_1$-$C_6$ alkoxy or $C_1$-$C_6$ haloalkyl groups.

17. The composition according to claim 15 wherein m is zero;

$R_1$ and $R_2$ are H;

$R_5$ is $C_1$-$C_3$ alkyl;

$R_6$ is H;

X is $CR_7R_8$;

$R_7$ and $R_8$ are each independently $C_1$-$C_4$ alkyl;

Z is $C_1$-$C_4$ alkyl;

p is 1;

G is $OR_{11}$, $S(O)_nR_{12}$,

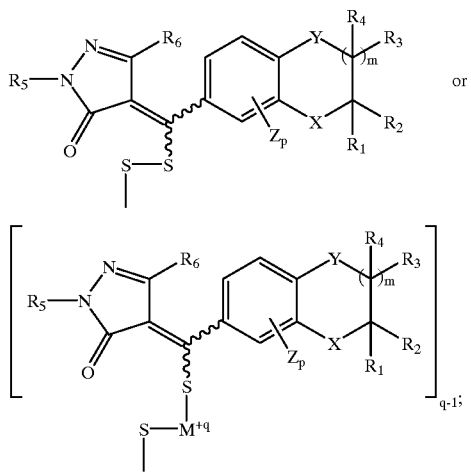

n is zero or 2;

$R_{11}$ is phenyl optionally substituted with one to three halogen, $C_1$-$C_2$ alkyl $C_1$-$C_3$ alkoxy or $C_1$-$C_3$ haloalkyl groups; and $R_{12}$ is $C_1$-$C_6$ alkyl.

18. The composition according to claim 15 wherein m is 1;

$R_1$, $R_2$, $R_3$ and $R_4$ are H;

$R_5$ is $C_1$-$C_3$ alkyl;

$R_6$ is H;

X is C=NOR$_{10}$;

$R_{10}$ is $C_1$-$C_6$ alkyl;

Z is $C_1$-$C_4$ alkyl;

p is 1;

G is OR$_{11}$, S(O)nR$_{12}$,

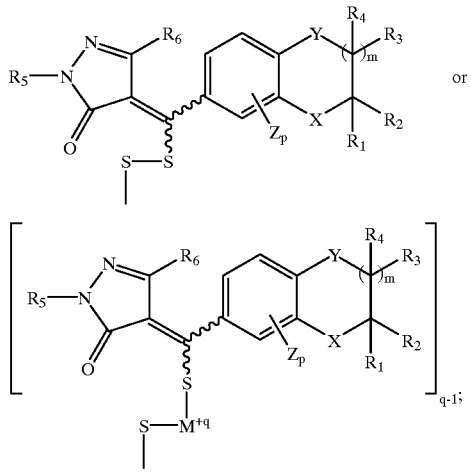

n is zero or 2;

$R_{11}$ is phenyl optionally substituted with one to three halogen, $C_1$-$C_2$ alkyl, $C_1$-$C_3$ alkoxy or $C_1$-$C_3$ haloalkyl groups; and $R_{12}$ is $C_1$-$C_6$ alkyl.

19. A process for the preparation of a compound of formula I

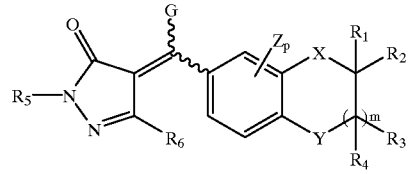

wherein m is zero or 1;

$R_1$, $R_2$, $R_3$ and $R_4$ are each, independently h, $C_1$-$C_4$ alkyl, $C_1$-$C_4$ haloalkyl or $C_2$-$C_4$ alkoxyalkyl;

$R_5$ is $C_1$-$C_3$ alkyl, $C_3$-$C_4$ alkenyl or $C_3$-$C_4$ haloalkenyl;

$R_6$ is H, halogen, CN, $C_1$-$C_4$ alkyl, $C_2$-$C_4$ alkenyl, $C_1$-$C_4$ alkoxyalkyl or $C_1$-$C_4$ alkoxycarbonyl;

X is CR$_{78}$, CHOR$_9$, C=NNR$_{16}$R$_{17}$, C=NOR$_{10}$, C=O or C(OR$_9$)$_2$;

$R_7$ is H, $C_1$-$C_4$ alkyl or $C_1$-$C_4$ haloalkyl;

$R_8$ is H, $C_1$-$C_4$ alkyl, $C_2$-$C_4$ alkenyl, $C_2$-$C_4$ alkynyl or $C_1$-$C_4$ alkoxyalkyl;

$R_9$ and $R_{10}$ are each, independently H or $C_1$-$C_6$ alkyl optionally substituted with one or more $C_2$-$C_6$ alkenyl, $C_2$-$C_6$ alkynyl, $C_1$-$C_6$ haloalkyl or $C_3$-$C_6$ cycloalkyl groups;

Y is O, S, SO or SO$_2$;

Z is H, halogen, $C_1$-$C_4$ alkyl, $C_1$-$C_4$ haloalkyl, $C_2$-$C_4$ alkoxyalkyl, $C_1$-$C_1$-$C_4$ alkoxy or $C_1$-$C_4$ haloalkoxy;

p is an integer of 1,2 or 3;

G is OR$_{11}$, S(O)$_7$R$_{12}$, NR$_{13}$R$_{14}$, P(O)(OR$_{15}$)$_2$ or halogen;

n is zero, 1 or 2;

$R_{11}$ and $R_{12}$ are each independently $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxyalkyl, benzyl optionally substituted with one to three halogen, $C_1$-$C_6$ alkyl, $C_1$-$C_6$ alkoxy or $C_1$-$C_6$ haloalkyl groups, or phenyl optionally substituted with one to three halogen, $C_1$-$C_6$ alkyl, $C_1$-$C_6$ alkoxy or $C_1$-$C_6$ haloalkyl groups;

$R_{13}$ and $R_{14}$ are each independently H, $C_1$-$C_6$ alkyl, $C_3$-$C_6$ alkenyl, $C_3$-$C_6$ alkynyl, or when $R_{13}$ and $R_{14}$ are taken together with the atoms to which they are attached, they represent a four- to seven- membered ring optionally interrupted by oxygen, sulfur, or nitrogen and optionally substituted with one to three halogen or $C_1$-$C_6$ alkyl groups;

$R_{15}$ is $C_1$-$C_6$ alkyl;

$R_{16}$ is H or $C_1$-$C_6$ alkyl;

$R_{17}$ is H, $C_1$-$C_6$ haloalkyl, $C_2$-$C_6$ aldoxycarbonyl, $C_2$-$C_6$ alkylcarbonyl, COR$_{18}$ or phenyl optionally substituted with one to three $C_1$-$C_3$ alkyl, halogen, CN or NO$_2$ groups, or $R_{16}$ and $R_{17}$ may be taken together to represent =C($C_1$-$C_3$ alkyl)$_2$; and $R_{18}$ is phenyl optionally substituted with one to three $C_1$-$C_3$ alkyl, halogen CH or NO$_2$ groups, which process comprises reacting an aroyl halide with a compound of formula II

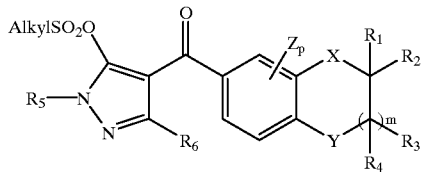

(II)

wherein $R_1$, $R_2$, $R_3$, $R_4$, $R_5$, $R_6$, X, Y, Z, m and p are as defined above to form a compound of formula I wherein G is halogen; and reacting said compund with at least one molar equivalent of one member selected from the group consisting of $R_{11}OH$, $R_{12}SH$, $R_{13}R_{14}NH$, $R_{16}R_{17}NNH_2$, and $PO(OR_{15})_3$, wherein $R_{11}$, $R_{12}$, $R_{13}$, $R_{14}$, $R_{15}$, $R_{16}$ and $R_{17}$ are defined hereinabove to form the desired formula I compound.

* * * * *

UNITED STATES PATENT AND TRADEMARK OFFICE
CERTIFICATE OF CORRECTION

PATENT NO. : 6,465,395 B2
DATED : October 15, 2002
INVENTOR(S) : Szucs et al.

It is certified that error appears in the above-identified patent and that said Letters Patent is hereby corrected as shown below:

Column 23,
Line 58, "$C_2$-$C_6$-haloalkyl" should be -- $C_2$-$C_6$-alkynyl, $C_1$-$C_6$-haloalkyl --.

Column 24,
Line 47, after "$C_2$-$C_6$-haloalkenyl" insert -- $C_2$-$C_6$-alkynyl --.
Line 59, "seven=membered" should be -- seven-membered --;
Lines 62 and 64, "$C_{1-C6}$ alkyl" should be -- $C_1$-$C_6$ alkyl --.

Column 25,
Line 10, "$C_{1-C4}$ alkyl" should be -- $C_1$-$C_4$ alkyl --;
Line 11, "$C_{1-C3}$ alkyl" should be -- $C_1$-$C_3$ alkyl --;
Line 12, "$C_{1-C4}$ alkyl" should be -- $C_1$-$C_4$ alkyl --;
Line 15, "$C_{1-C6}$ alkyl" should be -- $C_1$-$C_6$ alkyl --;
Lines 43-45, "$C_{1-C6}$ alkyl" should be -- $C_1$-$C_6$ alkyl -- in all four instances;
Line 49, "$C_{1-C3}$ alkyl" should be -- $C_1$-$C_3$ alkyl --;
Lines 52-53, "$C_{1-C4}$ alkyl" should be -- $C_1$-$C_4$ alkyl -- in both instances.

Column 26,
Line 18, "$C_{1-C2}$ alkyl, $C_{1-C3}$ alkoxy, or $C_{1-C3}$ haloalkyl" should be -- $C_1$-$C_2$ alkyl, $C_1$-$C_3$ alkoxy, or $C_1$-$C_3$ haloalkyl --;
Line 20, "$C_{1-C6}$ alkyl" should be -- $C_1$-$C_6$ alkyl --;
Line 24, "$C_{1-C3}$ alkyl" should be -- $C_1$-$C_3$ alkyl --;
Line 28, "$C_{1-C6}$ alkyl" should be -- $C_1$-$C_6$ alkyl --;
Line 29, "$C_{1-C4}$ alkyl" should be -- $C_1$-$C_4$ alkyl --;
Line 57, "$C_{1-C2}$ alkyl, $C_{1-C3}$ alkoxy, or $C_{1-C3}$ haloalkyl" should be -- $C_1$-$C_2$ alkyl, $C_1$-$C_3$ alkoxy, or $C_1$-$C_3$ haloalkyl --;
Line 59, "$C_{1-C6}$ alkyl" should be -- $C_1$-$C_6$ alkyl --.

Column 28,
Line 64, "$R_{10\ is\ C1}$-$C_6$-alkyl" should be -- $R_{10}$ is $C_1$-$C_6$ alkyl --.

UNITED STATES PATENT AND TRADEMARK OFFICE
CERTIFICATE OF CORRECTION

PATENT NO. : 6,465,395 B2
DATED : October 15, 2002
INVENTOR(S) : Szucs et al.

It is certified that error appears in the above-identified patent and that said Letters Patent is hereby corrected as shown below:

<u>Column 30,</u>
Line 53, "alkylor phenyl" should be -- alkyl or phenyl --.

Signed and Sealed this

Twenty-first Day of January, 2003

JAMES E. ROGAN
*Director of the United States Patent and Trademark Office*